(12) United States Patent
Chan et al.

(10) Patent No.: US 8,394,343 B2
(45) Date of Patent: Mar. 12, 2013

(54) INTEGRATED TEST STRIP CONTAINER WITH RETAINING INSERT

(75) Inventors: Frank A. Chan, Sunnyvale, CA (US); Matthew C. Sauers, Indianapolis, IN (US); Abner D. Joseph, Carmel, IN (US); Christopher Wiegel, Sunnyvale, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 372 days.

(21) Appl. No.: 12/768,036

(22) Filed: Apr. 27, 2010

(65) Prior Publication Data

US 2011/0263006 A1 Oct. 27, 2011

(51) Int. Cl.
*A61J 1/10* (2006.01)
*B01L 3/00* (2006.01)
*B01L 3/14* (2006.01)
*B01L 9/00* (2006.01)
*G01N 15/06* (2006.01)
*G01N 33/00* (2006.01)
*G01N 33/46* (2006.01)
*B65D 69/00* (2006.01)

(52) U.S. Cl. ....... 422/555; 422/68.1; 422/547; 422/550; 422/560; 206/569

(58) Field of Classification Search .............. 422/555; 206/256
See application file for complete search history.

(56) References Cited

U.S. PATENT DOCUMENTS

| | | | |
|---|---|---|---|
| 6,159,424 A | 12/2000 | Kauhaniemi et al. | |
| 6,343,693 B1 | 2/2002 | Finley | |
| 6,872,358 B2 | 3/2005 | Hagen et al. | |
| 6,908,008 B2 | 6/2005 | Pugh | |
| 6,997,343 B2 | 2/2006 | May et al. | |
| 7,516,847 B2* | 4/2009 | Henning | 206/569 |
| 8,236,254 B2* | 8/2012 | Myles et al. | 422/401 |
| 2003/0186446 A1 | 10/2003 | Pugh | |
| 2003/0212345 A1 | 11/2003 | McAllister et al. | |
| 2003/0223906 A1 | 12/2003 | McAllister et al. | |
| 2004/0173488 A1 | 9/2004 | Griffin et al. | |
| 2006/0278545 A1 | 12/2006 | Henning | |
| 2007/0144922 A1* | 6/2007 | Imoarai et al. | 206/204 |
| 2007/0264166 A1 | 11/2007 | West et al. | |
| 2008/0118400 A1* | 5/2008 | Neel et al. | 422/68.1 |
| 2011/0226643 A1* | 9/2011 | Kates et al. | 206/305 |

FOREIGN PATENT DOCUMENTS

| | | |
|---|---|---|
| WO | 02/078533 A2 | 10/2002 |
| WO | 03/082091 A2 | 10/2003 |
| WO | 2007/090662 A1 | 8/2007 |
| WO | 2008/101217 A2 | 8/2008 |

* cited by examiner

*Primary Examiner* — Jill Warden
*Assistant Examiner* — Charles D Hammond
(74) *Attorney, Agent, or Firm* — Dinsmore & Shohl LLP (57) ABSTRACT

A blood glucose meter for providing easy access to test strips and measuring blood glucose, a disposable and removable cartridge for providing easy access to test strips, and methods of manufacturing and utilization thereof are disclosed. The blood glucose meter for providing easy access to test strips and measuring blood glucose has a disposable and removable cartridge, a retaining member which releasably retains the test strips in a stacked configuration, and a housing. The disposable and removable cartridge has a rigid lid attached to a flexible body.

19 Claims, 7 Drawing Sheets

INTEGRATED TEST STRIP CONTAINER WITH RETAINING INSERT

TECHNICAL FIELD

Embodiments of the present invention relate generally to blood glucose meters, and particularly to blood glucose meters having a disposable and removable cartridge and to methods of manufacturing and utilization thereof.

BACKGROUND

The use of test strips in the determination of biological analyte concentration is of widespread importance, particularly to persons afflicted with type one diabetes. In regulating their disease, such diabetic patients may be required to perform an average of five to ten blood glucose tests per day via a process of self-monitoring to determine their blood glucose levels. As a result, diabetic patients expend a significant amount of time throughout their daily lives testing their blood glucose levels.

As the number of patients suffering from diabetes increases, the practice of self-monitoring blood glucose levels has become routine. The process of self-monitoring typically involves diabetic patients obtaining a test strip by removing it from a test strip container, applying a sample of blood thereto, inserting the test strip into a blood glucose meter, and obtaining results by measuring the concentration of analytes. When the test is completed, the test strip is removed from the meter and discarded.

Systems for monitoring blood glucose typically include a test strip container, a blood glucose meter, and a lancing pen with lancet; thus, the portability of current blood glucose monitoring systems is limited. Test strip containers commonly take the form of conventional vials wherein test strips recess below the vial opening and must be manually removed; these designs are often large in size and awkward in form, limiting portability. While some attempts have been made to incorporate test strips into a blood glucose meter, eliminating the need to carry a test strip vial, these designs carry with them a variety of disadvantages. Generally, the designs have been shown not to be robust in protecting the strips from the environment due to seal damage from repetitive use, i.e. multiple user closings and openings. Thus, additional embodiments for blood glucose meters and methods of manufacturing and utilization thereof are desirable.

SUMMARY

In one embodiment, the present invention relates to a blood glucose meter providing easy access to a test strip provided therewith and for measuring a blood glucose level of a blood sample provided to the test strip, comprising a disposable and removable cartridge having surfaces which define a resealable cavity containing the test strips and a housing accommodating a blood glucose measuring component and providing a receptacle. The disposable and removable cartridge has a retaining member which releasably retains the test strips in a stacked configuration. The housing accommodates a blood glucose measuring component which measures the blood glucose level of the blood sample when provided to the test strip which has been removed from among the test strips contained in the resealable cavity. The receptacle has surfaces which retain the disposable and removable cartridge with the housing.

In another embodiment, the present invention relates to a disposable and removable cartridge for providing easy access to test strips. The disposable and removable cartridge comprises a flexible body, a rigid lid attached to the flexible body, and a retaining member provided within the resealable cavity. The flexible body has surfaces which define a resealable cavity containing the test strips, the rigid lid has surfaces which abut with the surfaces of the flexible body for enclosing the resealable cavity, and the retaining member releasably retains the test strips in a stacked configuration. The disposable and removable cartridge for providing easy access to test strips has an open configuration and a closed configuration. The open configuration comprises the rigid lid being moved relative to the flexible body, such that the test strips are accessible in the cavity. The closed configuration comprises the rigid lid abutting with the flexible body, such that the test strips are sealed within the cavity.

In still another embodiment, the present invention relates to a method of manufacturing a blood glucose meter for providing easy access to test strips and measuring blood glucose, comprising providing a disposable and removable cartridge having surfaces which define a resealable cavity containing test strips and providing a housing accommodating a blood glucose measuring component and providing a receptacle. The disposable and removable cartridge has a retaining member which releasably retains the test strips in a stacked configuration. The housing accommodates a blood glucose measuring component for measuring a blood glucose level of a blood sample. The receptacle is integral with the blood glucose measuring component, wherein the receptacle has surfaces which retain the disposable and removable cartridge with the housing.

In yet still another embodiment, the present invention also relates to a method of providing easy access to test strips and measuring blood glucose which comprises utilizing the test strip container according to the present invention.

These and other features and advantages of these and other various embodiments according to the present invention will become more apparent in view of the drawings, detailed description, and claims provided that follow hereafter.

BRIEF DESCRIPTION OF THE DRAWINGS

The following detailed description of the embodiments of the present invention can be best understood when read in conjunction with the following drawings, where like structure is indicated with like reference numerals, and in which.

Skilled artisans appreciate that elements in the figures are illustrated for simplicity and clarity and have not necessarily been drawn to scale. For example, the dimensions of some of the elements in the figures may be exaggerated relative to other elements, as well as conventional parts removed, to help to improve understanding of the various embodiments of the present invention.

DETAILED DESCRIPTION

The following terms are used in the present application:

The term "stacked configuration" is used herein to refer to a configuration of the test strips wherein all of the test strips releasably retained by the retaining member overlap, such that they are arranged in a substantially upright pile, i.e. a deck of cards configuration.

In the context of a disposable and removable cartridge, the term "rigid lid" is used herein to refer to a lid that is configured to provide physical protection to test strips contained within a cavity of the disposable and removable cartridge.

The term "flexible body" is used herein to refer to a body that is configured to provide environmental protection to test strips contained within the cavity of the disposable and removable cartridge.

The term "gusseted bag" is used herein to refer to a bag-like material which has folds in the sidewalls.

Embodiments of the present invention relate to a disposable and removable cartridge comprising a flexible body having surfaces which define a resealable cavity containing the test strips, a rigid lid attached to the flexible body and having surfaces which abut with the surfaces of the flexible body for enclosing the resealable cavity, and a retaining member provided within the resealable cavity and releasably retaining the test strips in a stacked configuration. The disposable and removable cartridge has an open configuration and a closed configuration.

Embodiments of the present invention also relate to a blood glucose meter providing easy access to a test strip provided therewith and for measuring a blood glucose level of a blood sample provided to the test strip. The blood glucose meter comprises a disposable and removable cartridge having surfaces which define a resealable cavity containing the test strips, and a housing accommodating a blood glucose measuring component which measures the blood glucose level of the blood sample when provided to the test strip which has been removed from among the test strips contained in the resealable cavity, and providing a receptacle having surfaces which retain a disposable and removable cartridge with the housing. Embodiments of the present invention also relate to methods of manufacturing and to utilization thereof.

Figure 1:
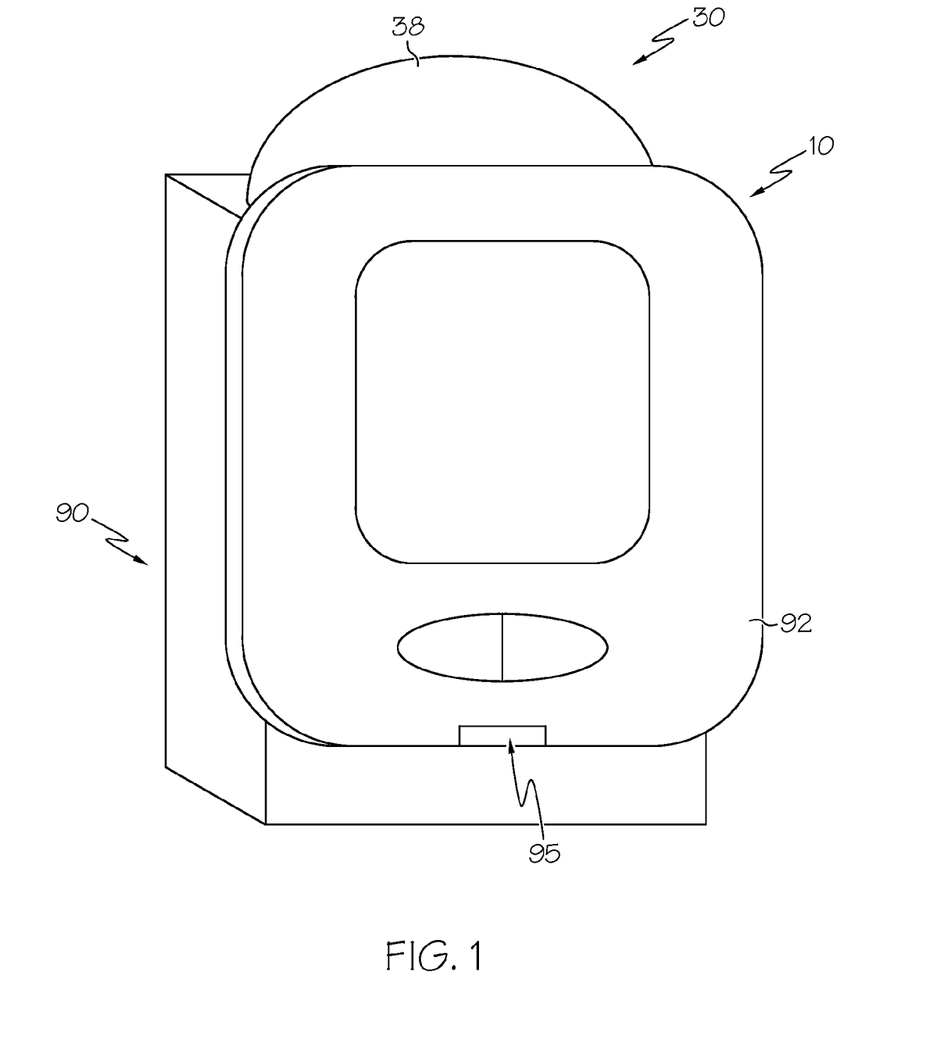
FIG. 1 is a front perspective view of a blood glucose meter with a disposable and removable cartridge in a closed configuration according to an embodiment of the present invention.
Figure 2:
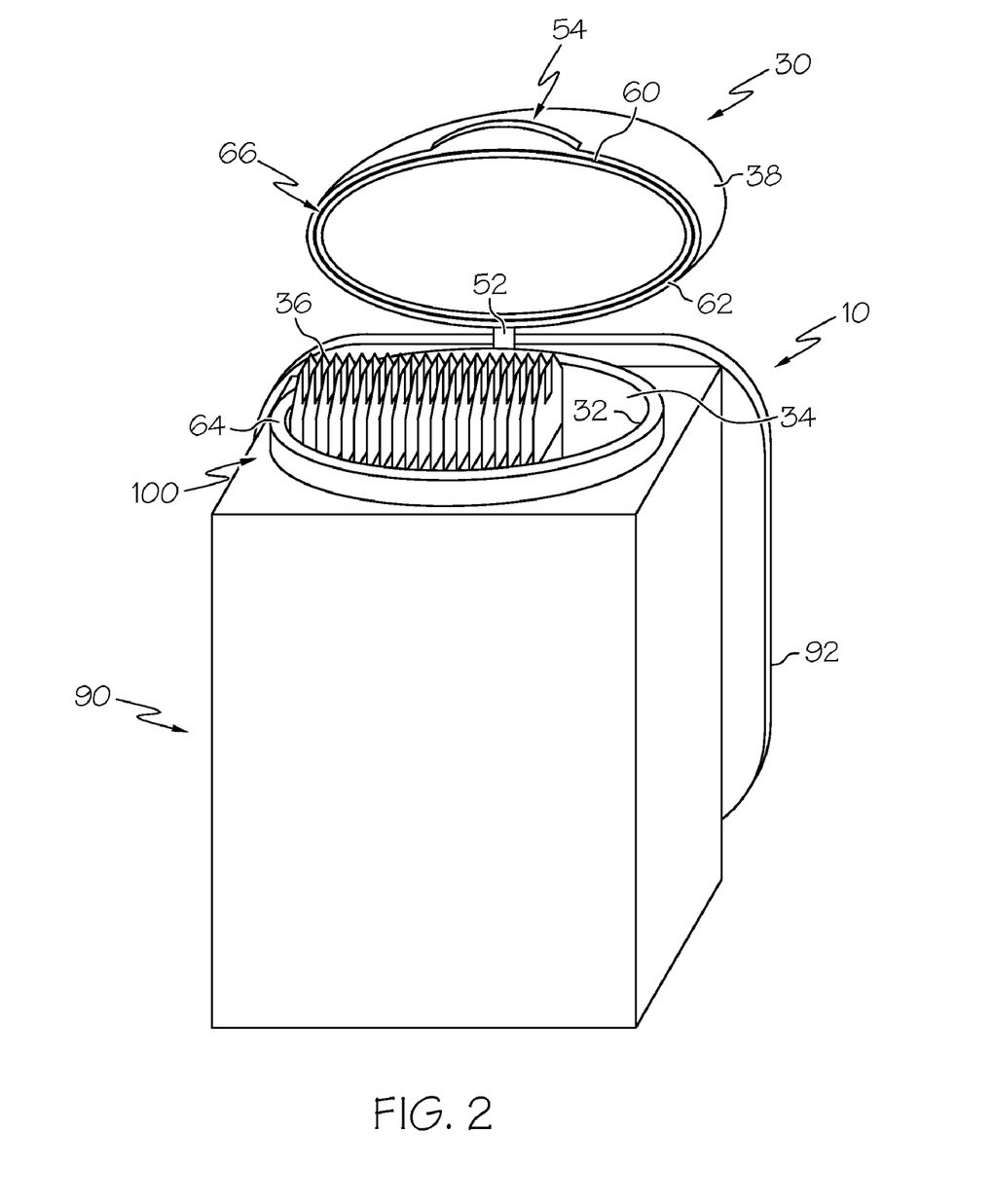
FIG. 2 is a back perspective view of a blood glucose meter with a disposable and removable cartridge in an open configuration according to an embodiment of the present invention.

As shown in FIGS. 1 and 2, in one embodiment, the blood glucose meter 10 of the present invention has a disposable and removable cartridge 30. The disposable and removable cartridge 30 has surfaces 32 which define a resealable cavity 34 containing test strips 36. The disposable and removable cartridge 30 provides physical and environmental protection to the test strips 36.

Figure 3:
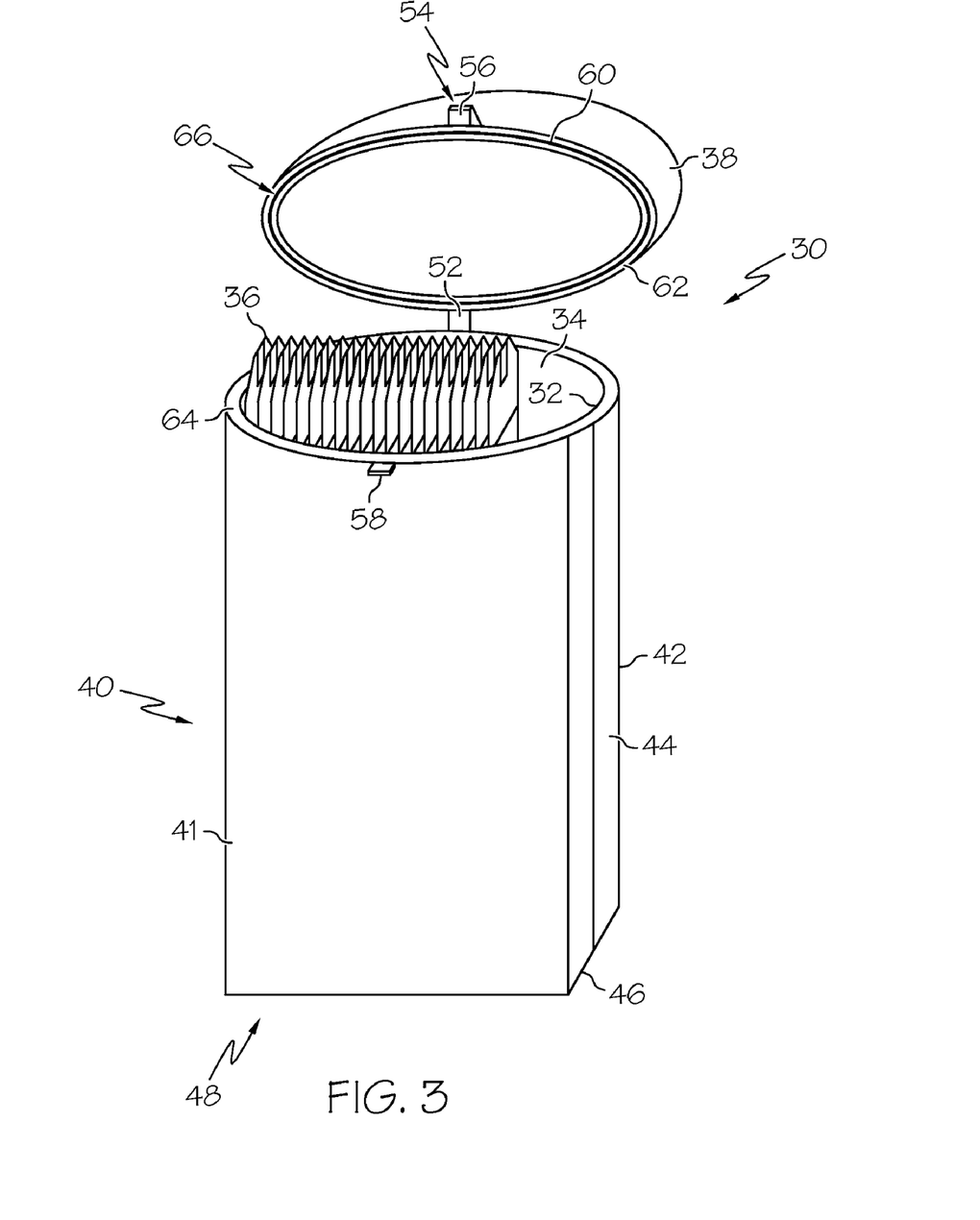
FIG. 3 is a front perspective view of a disposable and removable cartridge in an open configuration according to an embodiment of the present invention.
Figure 4:
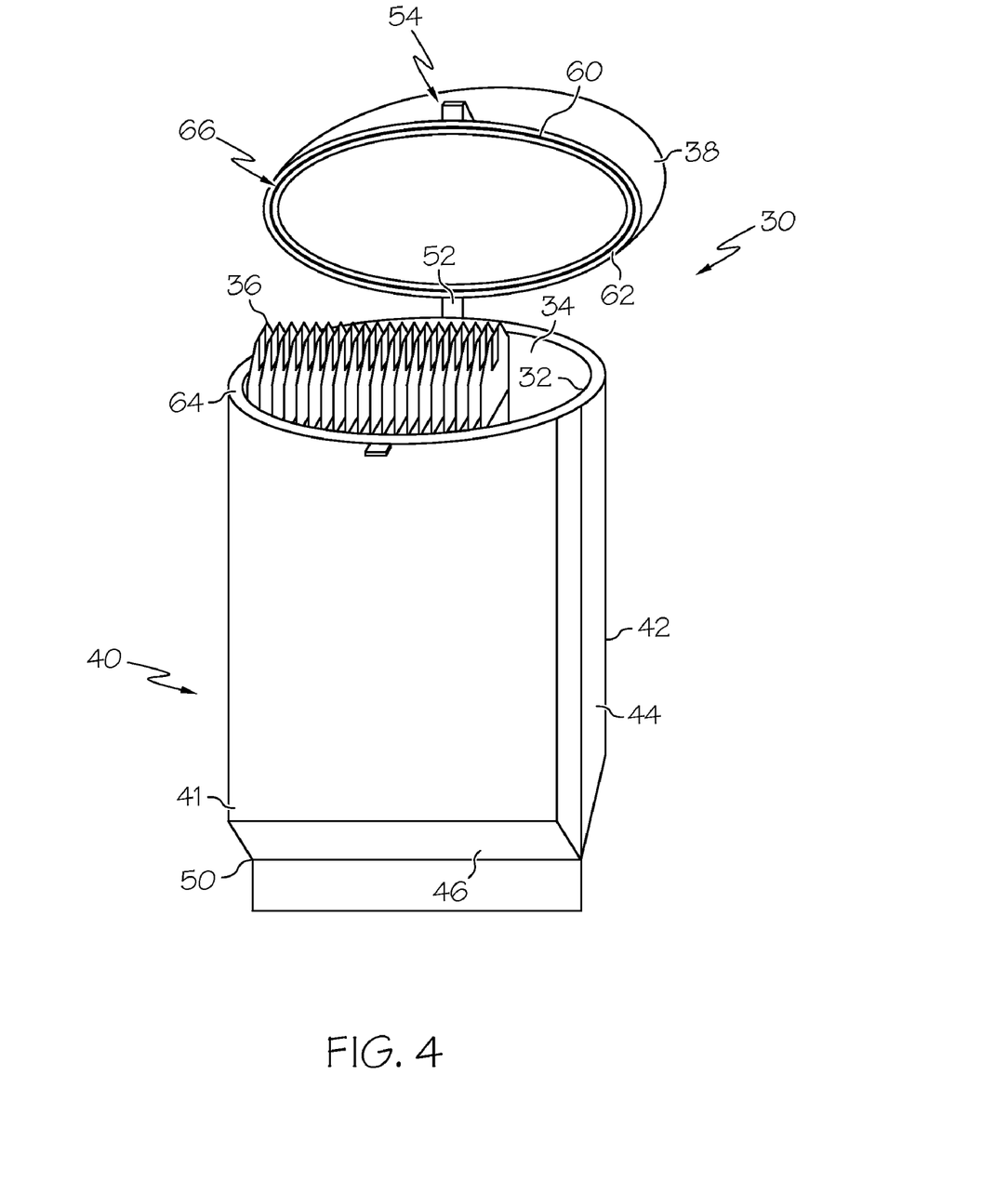
FIG. 4 is a front perspective view of a disposable and removable cartridge wherein the sealable base has been heat sealed according to an embodiment of the present invention.

As shown in FIGS. 3 and 4, in one aspect of this embodiment, the disposable and removable cartridge 30 has a rigid lid 38 attached to a flexible body 40. In this aspect, the surfaces 32 are provided by the rigid lid 38 attached to the flexible body 40. In one particular aspect, the rigid lid 38 is configured to provide physical protection to the test strips 36 contained within the resealable cavity 34 of the disposable and removable cartridge 30. More particularly, the rigid lid 38 is configured to be resistant to bending and/or deformation, such that it protects the test strips 36 contained within the resealable cavity 34 from bending, tearing, and/or deforming. In this way, the rigid lid 38 preserves the physical structure of the test strips 36 such that the test strips 36 may be used by test strip users to accurately measure blood glucose levels.

In one particular aspect, the rigid lid 38 comprises plastics, polymers, rubbers, metals, composites and/or alloys. In a further aspect, the rigid lid 38 comprises polypropylene and/or polyethylene. In still a further aspect, the rigid lid 38 comprises polypropylene. However, the rigid lid 38 should not be limited to the materials disclosed herein, but may comprise any material capable of providing physical protection to the test strips 36 contained within the resealable cavity 34.

In another aspect of this embodiment, the disposable and removable cartridge 30 has a flexible body 40. The flexible body 40 is configured to provide environmental protection to the test strips 36 contained within the resealable cavity 34 of the disposable and removable cartridge 30. More particularly, the flexible body 40 is configured to provide a barrier against environmental contaminants such as moisture and/or particulates. In this way, the flexible body 40 substantially excludes environmental contaminants from contacting the test strips 36 contained within the resealable cavity 34, such that the test strips 36 may be used by test strip users to accurately measure blood glucose levels.

In one particular aspect, the flexible body 40 comprises a thin material. In a further aspect, the flexible body 40 is configured such that it has a low permeability to moisture. In still a further aspect, the flexible body 40 comprises a moisture barrier film. In yet still a further aspect, the flexible body 40 comprises an aluminized foil layer. In one particular aspect, the aluminized foil layer provides a moisture barrier. In a further aspect, the flexible body 40 comprises a thermoplastic resin layer. In still a further aspect, the thermoplastic resin layer comprises polyethylene terephthalate ("PET"). In one particular aspect, the thermoplastic resin layer provides a hermetic seal. However, the flexible body 40 should not be limited to the configurations disclosed herein, however, but may comprise any configuration wherein the flexible body 40 protects test strips 36 from environmental contaminants by providing a barrier against environmental contaminants.

Figure 5A:
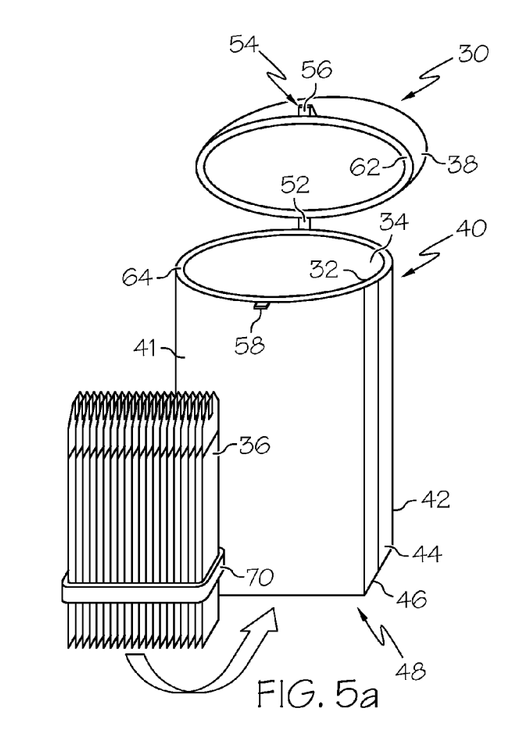
FIG. 5a is a front perspective view which depicts loading test strips into an opening defined by a disposable and removable cartridge according to an embodiment of the present invention.
Figure 5B:
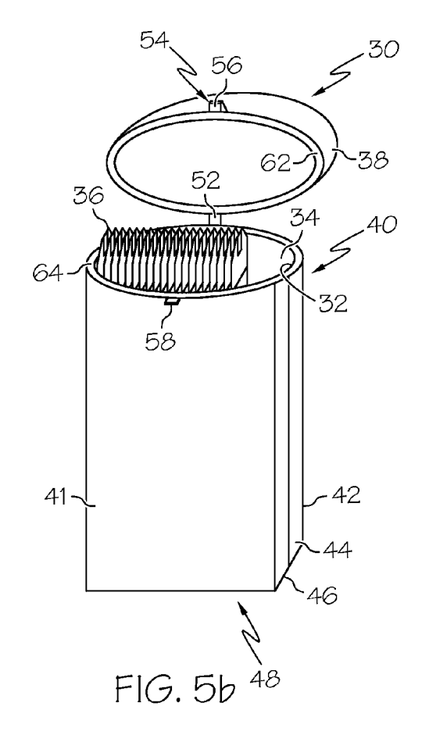
FIG. 5b is a front perspective view of the disposable and removable cartridge of FIG. 5a in the open configuration with test strips loaded therein.
Figure 5C:
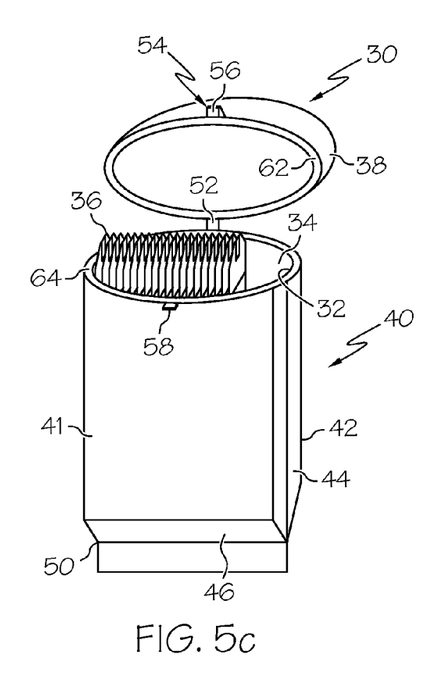
FIG. 5c is a front perspective view of the disposable and removable cartridge of FIG. 5b wherein the sealable base has been heat sealed.
Figure 6:
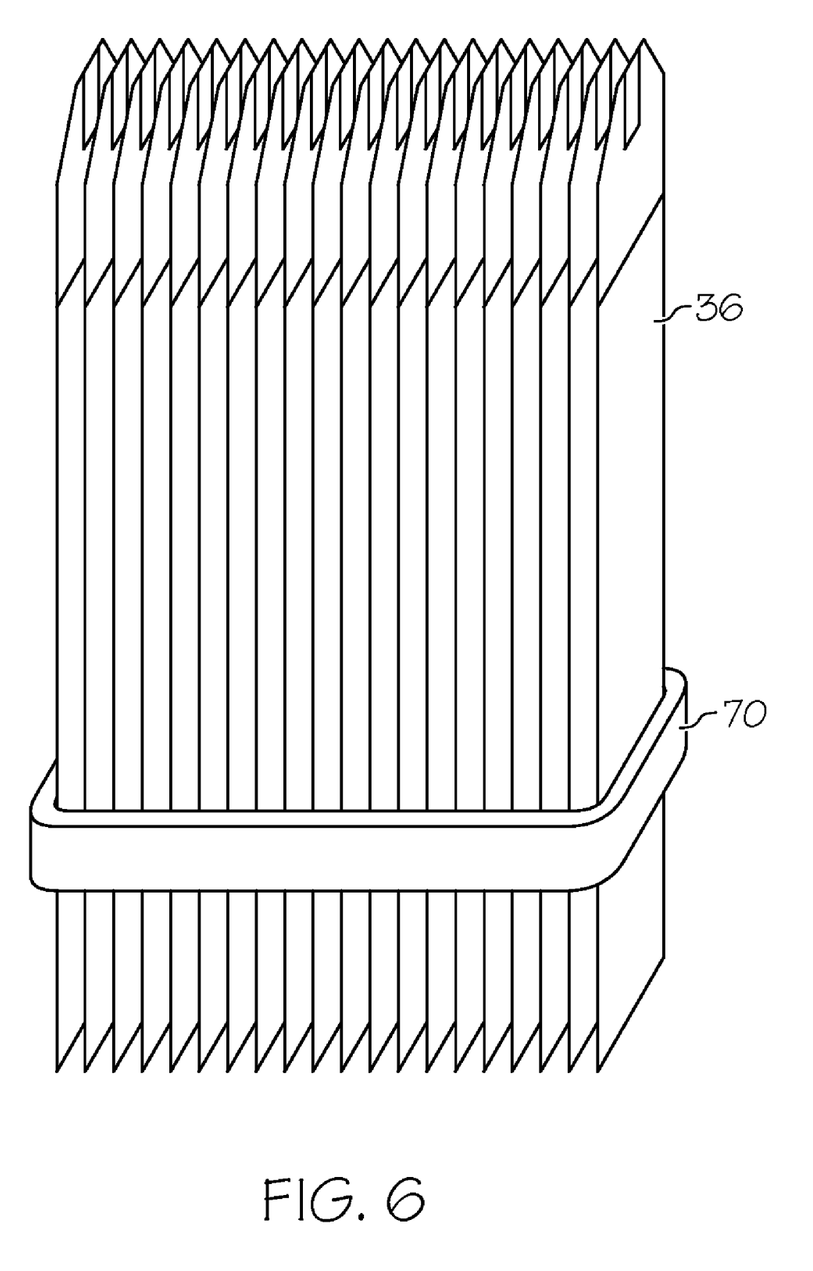
FIG. 6 is a side perspective view of a retaining member which releasably retains test strips in a stacked configuration according to an embodiment of the present invention.

Referring to FIGS. 3, 4, 5a, 5b, and 5c, in one particular aspect, the flexible body 40 defines a gusseted bag. The gusseted bag comprises a front wall 41, a back wall 42, inward-folded, substantially V-shaped folds at opposing sidewalls 44 (same as the unshown sidewall) and a sealable base 46. In one aspect, the sealable base 46 extends around the bottom perimeter of the front and back walls, 41, 42, and the opposing sidewalls 44. In one aspect, the sealable base 46 defines an opening 48 such that the test strips 36 are loaded into the disposable and removable cartridge 30 through the opening 48 defined by the sealable base 46, as indicated in FIGS. 5a and 5b. In a further aspect, the sealable base 46 is heat sealed after loading the test strips 36 through the open sealable base 46, such that the opening 48 is enclosed, as indicated in FIG. 5c. In this aspect, the heat seal creates a hermetically resealable disposable and removable cartridge 30 (in the closed configuration), which provides environmental protection to the test strips 36 contained within the resealable cavity 34. In a further aspect, the heat seal creates a hermetically resealable disposable and removable cartridge 30, such that upon engaging the closed configuration after engaging the open configuration, the disposable and removable cartridge 30 is hermetically sealed.

The sealable base 46 may be heat sealed with a heat sealing device. The heat sealing device operates to fuse the sealable base 46 such that the resealable cavity 34 is enclosed upon the application of heat. Upon heat sealing, the sealable base 46 defines a heat seal line 50. Suitable heat sealing devices include but are not limited to continuous heat sealers, impulse heat sealers, hot bar sealers, induction sealers, and/or ultrasonic welders. In one particular aspect, the heat sealing device is an ultrasonic welder, wherein a heat seal (i.e. heat weld) is created by the application of high-frequency ultrasonic acoustic vibrations. However, the heat sealing devices should not be limited to those disclosed herein, but may include any heat sealing device capable of fusing (i.e. welding) the sealable base 46 upon the application of heat.

Referring to FIGS. 3 and 4, in a further aspect, the rigid lid 38 is hingedly attached to the flexible body 40. In one aspect, the rigid lid 38 is hingedly attached to the flexible body 40 with a hinging mechanism 52. The hinging mechanism 52 may include a pin in hole mechanism or a living hinge mechanism. However, the hinging mechanism 52 should not be limited to those disclosed herein, but may include any hinging mechanism such that the rigid lid 38 may translate about its attachment to the flexible body 40. In an alternative aspect, the rigid lid 38 is attached to the flexible body 40 such that the rigid lid 38 releasably engages the flexible body 40. In this particular aspect, the rigid lid 38 may be wholly separated from the flexible body 40.

As shown in FIGS. 2, 3, and 4, in one particular aspect of this embodiment, the disposable and removable cartridge 30 comprises an open configuration, wherein the rigid lid 38 is movable relative to the flexible body 40. In one aspect, the open configuration comprises the rigid lid 38 moving about its attachment to the flexible body 40 such that the test strips 36 are accessible in the resealable cavity 34. In this particular aspect, the rigid lid 38 is not wholly separated from the flexible body 40. In an alternative aspect, the open configuration comprises the rigid lid 38 being wholly separated from the flexible body 40 such that the test strips 36 are accessible in the resealable cavity 34.

As shown in FIG. 1, in another aspect, the disposable and removable cartridge 30 has a closed configuration. In one particular aspect, the closed configuration comprises the surfaces of the rigid lid 38 abutting with the surfaces of the flexible body 40, such that the test strips 36 are sealed within the resealable cavity 34. In this way, the closed configuration may be exploited to protect the test strips 36 within the resealable cavity 34 from moisture and other environmental contaminants when the test strips 36 are not required for testing.

In one particular aspect, the disposable and removable cartridge 30 comprises a fastening mechanism 54 such that the disposable and removable cartridge 30 may be releasably fixed in the closed configuration. In a further aspect, the fastening mechanism 54 is a latching mechanism comprising upper and lower releasably mating parts 56, 58, either mechanically or magnetically based. Alternatively, the fastening mechanism 54 may comprise a clamping mechanism or a snap-fit mechanism. In one particular aspect wherein the fastening mechanism 54 is a snap-fit mechanism, the rigid lid 38 may further comprise a thumb tab.

As shown in FIGS. 2, 3, and 4, in another aspect, the disposable and removable cartridge 30 has a seal 60. The seal 60 provides a barrier against contaminants such as moisture and/or particulates. In this particular aspect, the seal 60 excludes contaminants in multiple capacities, i.e. the seal 60 excludes contaminants from the area in between the rigid lid 38 and the flexible body 40, and the seal 60 excludes contaminants from the area in between the disposable and removable cartridge 30 and the housing (not shown). In this way, the seal 60 protects the test strips 36 from contamination such that the test strips 36 may be used by test strip users to accurately measure blood glucose levels.

The seal 60 may be attached to and/or adhered to the disposable and removable cartridge 30. In one aspect, the seal 60 may be attached to and/or adhered to the rigid lid 38 of the disposable and removable cartridge 30. In a further aspect, the rigid lid 38 comprises an inner rim 62. In this particular aspect, the seal 60 is adhered to the inner rim 62. In another aspect, the seal 60 may be attached to and/or adhered to the flexible body 40 of the disposable and removable cartridge 30. In one particular aspect, the disposable and removable cartridge 30 has a rigid rim 64. In this particular aspect, the seal 60 may be attached to and/or adhered to the rigid rim 64 of the flexible body 40.

In one aspect of this embodiment, the rigid rim 64 is configured to increase the robustness of the seal. Additionally, the rigid rim 64 is configured to provide a robust surface wherein the disposable and removable cartridge 30 is retained with the housing 90. In one particular aspect, the rigid rim 64 comprises plastics, polymers, rubbers, metals, composites and/or alloys. In a further aspect, the rigid rim 64 comprises polypropylene and/or polyethylene. In still a further aspect, the rigid rim 64 comprises polypropylene. Generally, the rigid rim 64 comprises the same material as the rigid lid 38. The rigid rim 64 extends around the top, inner perimeter of the flexible body 40. In one particular aspect, the rigid lid 38 is hingedly attached to the rigid rim 64. In a further aspect, the rigid lid 38 is attached to the rigid rim 64 such that a seal is created via interference fit, i.e. a stopper in bottle-like configuration. In another aspect, the rigid rim 64 is overmolded with a thermoelastomer creating a seal, i.e. a gasket-like configuration. In an alternative embodiment, the rigid lid 38 may releasably engage the rigid rim 64.

The area wherein the seal 60 is attached to and/or adhered to the disposable and removable cartridge 30 is referred to as the seal line 66. In one particular aspect, the seal line 66 is reinforced to increase durability and to provide a more robust seal. The seal line 66 may be reinforced with plastics and/or polymers to increase the durability of the disposable and removable cartridge 30.

In one particular aspect, the rigid lid 38 is substantially ovular and the rigid rim 64 is substantially ovular in shape. However, the shape of the rigid lid 38 and the rigid rim 64 should not be limited to substantially ovular, but may comprise any shape such that the rigid lid 38 may abut with the rigid rim 64 to enclose the cavity, and such that the disposable and removable cartridge 30 may be retained with the housing (not shown).

As shown in FIGS. 5a, 5b, 5c, and 6, in yet another aspect of this embodiment, the disposable and removable cartridge 30 has a retaining member 70 which releasably retains the test strips 36 in a stacked configuration. The retaining member 70 may comprise an elastic biasing member, a molded frame, and/or retaining clip. In one particular aspect, the retaining member 70 comprises an elastic biasing member. In this particular aspect, the elastic biasing member releasably retains the test strips 36 via a biasing force which releasably clamps, squeezes or holds the test strips 36 together. Also in this particular aspect, the elastic biasing member releasably retains the test strips 36 such that upon removal of a test strip 36 by a test strip user, the elastic biasing member releasably clamps, squeezes or holds the remaining test strips 36 together. However, the retaining member 70 should not be limited to the configurations disclosed herein, but may include any retaining member 70 which releasably retains the test strips 36 in a stacked configuration. Moreover, in one particular aspect, the retaining member 70 may comprise a desiccant to absorb moisture.

Figure 7:
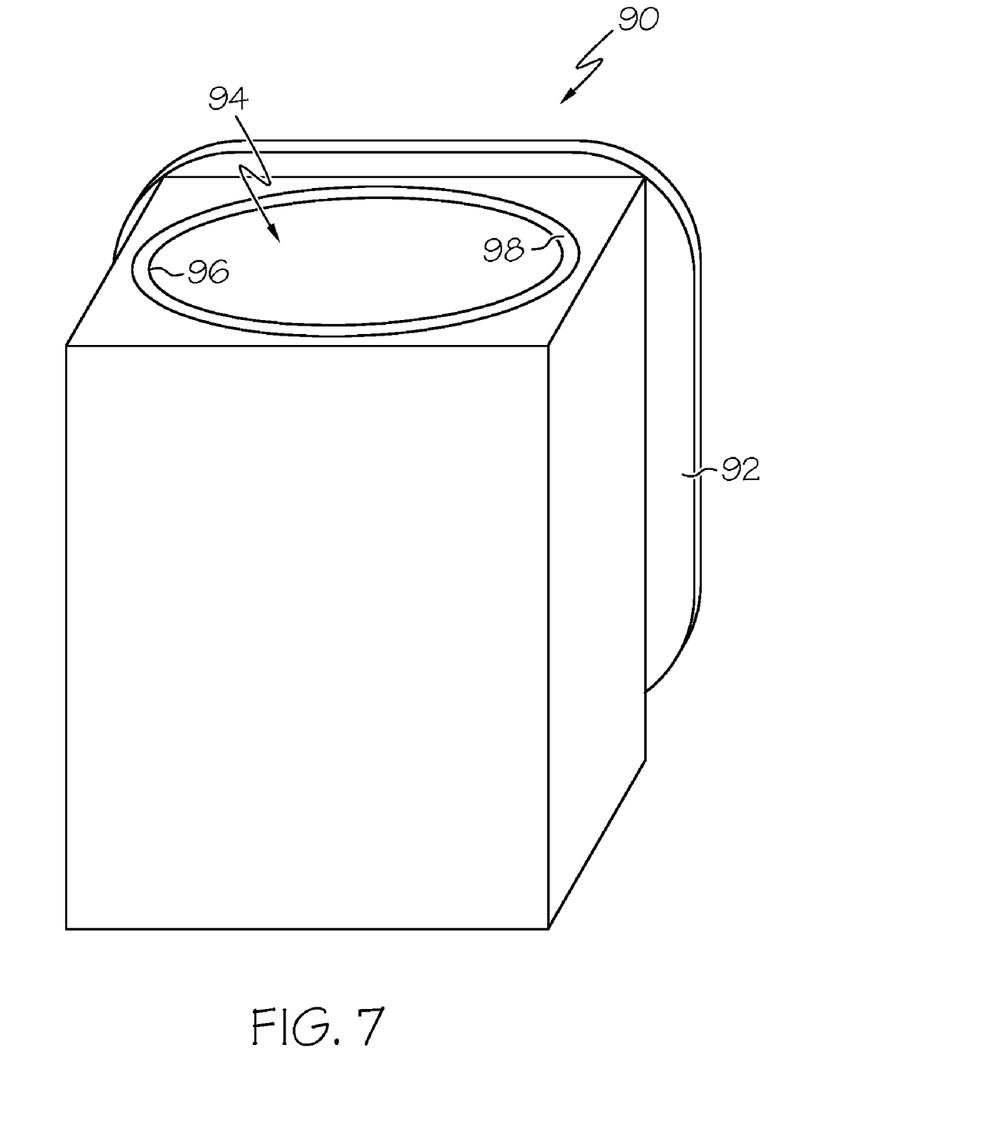
FIG. 7 is a back perspective view of a housing of a blood glucose meter according to an embodiment of the present invention.

As shown in FIGS. 1, 2, and 7, in yet another aspect of this embodiment, the blood glucose meter 10 comprises a housing 90 accommodating a blood glucose measuring component 92 for measuring a blood glucose level of a blood sample. In one particular aspect, the blood glucose measuring component 92 comprises a test strip port 95. The test strip port 95 may be sized to receive a test strip 36 for testing a blood sample. An example of a suitable blood glucose measuring component 92 includes the blood glucose measuring device described in U.S. patent application Ser. No. 12/486,805, the contents of which are hereby incorporated by reference. Examples of test strips 36 suitable for use with the blood glucose measuring device 92 include those described in U.S. Pat. Nos. 6,193,873; 6,475,372; 6,716,577; 6,620,310; and 6,558,528, the contents of which are hereby incorporated by reference.

The blood glucose measuring component 92 may be accommodated by the housing 90 such that it is attachable to the housing 90 or integral with the housing 90. In one aspect, the blood glucose measuring component 92 is attachable to the housing 90 via a snap-fit mechanism, an interference fit mechanism, or a latching mechanism (not shown). In a further aspect, the latching mechanism may comprise a latch and hook. In an alternative aspect, the blood glucose measuring component 92 is integral with the housing 90 such that it is co-molded with the housing 90.

Still referring to FIGS. 1, 2, and 7, in yet another aspect of this embodiment, the housing 90 provides a receptacle 94 having surfaces 96 and a disposable and removable cartridge-engaging rim 98 which retain the disposable and removable cartridge 30 with the housing 90. In one particular aspect, the disposable and removable cartridge 30 is retained with the housing such that substantially all of the flexible body 40 is disposed within the receptacle 94. In this particular aspect, the rigid lid 38 is exposed to the ambient environment.

In a further aspect, the disposable and removable cartridge 30 is retained with the housing 90 with a fastening device 100. The fastening device 100 may comprise a snap-fit mechanism, an interference fit mechanism, or a latching mechanism. In one particular aspect, the fastening device 100 is a snap-fit mechanism, wherein the rigid rim 64 of the flexible body 40 snaps onto the disposable and removable cartridge-engaging rim 98, such that the disposable and removable cartridge 30 is releasably retained with the housing 90. Alternatively, the fastening device 100 may retain the disposable and removable cartridge 30 with the housing with latches and hooks, detents and ribs, and/or magnets. However, the fastening device 100 should not be limited to the mechanisms disclosed herein, but may comprise any mechanism capable of releasably retaining the disposable and removable cartridge 30 with the housing 90.

In another embodiment, a method of providing easy access to test strips 36 and measuring blood glucose which comprises utilizing a blood glucose meter 10 according to the present invention is also disclosed.

In still another embodiment, the present invention relates to a method of manufacturing a blood glucose meter 10 for providing easy access to test strips 36 and measuring blood glucose. The method comprises providing a disposable and removable cartridge 30 and providing a housing 90. The disposable and removable cartridge 30 has surfaces 32 which define a resealable cavity 34 containing test strips 36 wherein the disposable and removable cartridge 30 has a retaining member 70 which releasably retains the test strips 36 in a stacked configuration. The housing 90 accommodates a blood glucose measuring component 92 for measuring a blood glucose level of a blood sample and provides a receptacle 94 having surfaces 96 which retain the disposable and removable cartridge 30 with the housing 90.

For the purposes of describing and defining the present invention it is noted that the terms "about" and "substantially" are utilized herein to represent the inherent degree of uncertainty that may be attributed to any quantitative comparison, value, measurement, or other representation. The terms "about" and "substantially" are also utilized herein to represent the degree by which a quantitative representation may vary from a stated reference without resulting in a change in the basic function of the subject matter at issue.

The above description and drawings are only to be considered illustrative of exemplary embodiments, which achieve the features and advantages of the present invention. Modification and substitutions the features and steps described can be made without departing from the intent and scope of the present invention. Accordingly, the invention is not to be considered as being limited by the foregoing description and drawings, but is only limited by the scope of the appended claims.

What is claimed is:

1. A removable cartridge for an integrated strip container and blood glucose meter, comprising:
   a flexible body comprising a moisture barrier film and a resealable cavity for containing the test strips;
   a rigid lid attached to a top upper perimeter of the flexible body; and
   strips provided within the cavity with a retaining member releasably retaining the test strips in an upright and stacked configuration, wherein the removable cartridge has an open configuration and a closed configuration, in which:
      the open configuration comprises the rigid lid being moved relative to the flexible body, such that the strips are accessible in the cavity, and
      the closed configuration comprises the rigid lid abutting surfaces at the top upper perimeter of the flexible body defining a seal, such that the strips are sealed within in the cavity.

2. The removable cartridge of claim 1, wherein the rigid lid is attached to the flexible body with a hinging mechanism.

3. The removable cartridge of claim 1, wherein the flexible body comprises a gusseted bag having a front wall, a back wall, inward-folded, substantially V-shaped folds at opposing sidewalls, and a sealed base.

4. The removable cartridge of claim 3, wherein the base is heat sealed.

5. The removable cartridge of claim 1, further comprising a fastening mechanism to releasably fix the removable cartridge in the closed configuration.

6. The removable cartridge of claim 1, wherein the retaining member comprises an elastic biasing member.

7. A method of manufacturing a blood glucose meter for providing easy access to test strips and measuring blood glucose, comprising:
   providing a removable cartridge comprising a flexible body comprising a moisture barrier film and a resealable cavity containing test strips provided within the cavity in an upright and stacked configuration by a retaining member, the removable cartridge further comprising a rigid lid attached to a top upper perimeter of the flexible body; and providing a housing comprising a blood glucose measuring component for measuring a blood glucose level of a blood sample and a receptacle configured to retain the and removable cartridge with the housing.

8. An integrated strip container and blood glucose meter, comprising:

a housing comprising a measuring component and a receptacle; and a removable cartridge comprising a flexible body comprising a moisture barrier film and a rigid lid hingedly attached to a rigid rim mounted at a top inner perimeter of the flexible body and defining access to a cavity configured to receive a plurality of strips, the receptacle configured to receive and retain the removable cartridge therein, the rigid lid configured to define a seal for excluding contaminants when the rigid lid is in a releasable engagement with the rigid rim.

9. The integrated strip container and blood glucose meter of claim 8, wherein the flexible body comprises a gusseted bag.

10. The integrated strip container and blood glucose meter of claim 9, wherein the gusseted bag is heat sealed at a base thereof.

11. The integrated strip container and blood glucose meter of claim 8, wherein the rigid lid is movable relative to the flexible body to provide an open configuration for providing access to strips in the cavity.

12. The integrated strip container and blood glucose meter of claim 8, wherein the removable cartridge is retained with the housing such that substantially all of the flexible body is disposed within the receptacle.

13. The integrated strip container and blood glucose meter of claim 8, wherein the removable cartridge is retained with the housing with a fastening device.

14. The integrated strip container and blood glucose meter of claim 8, wherein the strips are provided to the cavity and stacked configuration by a retaining member comprising an elastic biasing member.

15. The integrated strip container and blood glucose meter of claim 8, the measuring component being releasably attachable to the housing having the receptacle.

16. The integrated strip container and blood glucose meter of claim 8, the measuring component being integral with the housing having the receptacle.

17. The integrated strip container and blood glucose meter of claim 16, the housing and measuring component being co-molded.

18. The integrated strip container and blood glucose meter of claim 8, further comprising a fastening mechanism configured to latch the rigid lid to the rigid rim for maintaining the seal.

19. The integrated strip container and blood glucose meter of claim 18, the fastening mechanism comprising one of a latching mechanism comprising upper and lower releasably mating parts for mechanical or magnetic latching, a clamping mechanism, and a snap-fit mechanism comprising a thumb tab.

* * * * *

UNITED STATES PATENT AND TRADEMARK OFFICE
CERTIFICATE OF CORRECTION

PATENT NO.         : 8,394,343 B2
APPLICATION NO.    : 12/768036
DATED              : March 12, 2013
INVENTOR(S)        : Frank A. Chan et al.

It is certified that error appears in the above-identified patent and that said Letters Patent is hereby corrected as shown below:

In the Claims

Col. 10, Claim 14, Line 9, "to the cavity and stacked configuration" should read
--to the cavity in an upright and stacked configuration--.

Signed and Sealed this
Twenty-fifth Day of March, 2014

Michelle K. Lee
*Deputy Director of the United States Patent and Trademark Office*